United States Patent
Schmieding et al.

(10) Patent No.: US 8,409,250 B2
(45) Date of Patent: Apr. 2, 2013

(54) MENISCAL REPAIR SYSTEM AND METHOD (75) Inventors: Reinhold Schmieding, Naples, FL (US); R. D. Grafton, Naples, FL (US)

(73) Assignee: Arthrex, Inc., Naples, FL (US)

( * ) Notice: Subject to any disclaimer, the term of this patent is extended or adjusted under 35 U.S.C. 154(b) by 1829 days.

(21) Appl. No.: 10/349,099

(22) Filed: Jan. 23, 2003

(65) Prior Publication Data
US 2003/0139754 A1    Jul. 24, 2003

Related U.S. Application Data
(60) Provisional application No. 60/350,029, filed on Jan. 23, 2002.

(51) Int. Cl.
A61B 17/00 (2006.01)
(52) U.S. Cl. ........................................ 606/232
(58) Field of Classification Search ................. 606/104, 606/144, 72, 75, 219
See application file for complete search history.

(56) References Cited

U.S. PATENT DOCUMENTS

| | | | |
|---|---|---|---|
| 3,211,199 A * | 10/1965 | Reed ............................... | 81/460 |
| 3,800,783 A | 4/1974 | Jamshidi | |
| 3,892,232 A * | 7/1975 | Neufeld ........................... | 606/80 |
| 4,175,555 A | 11/1979 | Herbert | |
| 4,507,817 A | 4/1985 | Staffeld | |
| 4,532,926 A | 8/1985 | O'Holla | |
| 4,873,976 A | 10/1989 | Schreiber | |
| 4,884,572 A | 12/1989 | Bays et al. | |
| 4,895,148 A | 1/1990 | Bays et al. | |
| 4,924,865 A | 5/1990 | Bays et al. | |
| 4,976,715 A | 12/1990 | Bays et al. | |
| 5,059,206 A | 10/1991 | Winters | |
| 5,129,906 A | 7/1992 | Ross et al. | |
| 5,236,431 A * | 8/1993 | Gogolewski et al. ........... | 606/72 |
| 5,261,914 A | 11/1993 | Warren | |
| 5,342,376 A | 8/1994 | Ruff | |
| 5,364,400 A | 11/1994 | Rego, Jr. et al. | |
| 5,398,861 A * | 3/1995 | Green .......................... | 227/175.1 |
| 5,464,407 A * | 11/1995 | McGuire ........................ | 606/86 |
| 5,466,243 A * | 11/1995 | Schmieding et al. .......... | 606/232 |
| 5,520,696 A * | 5/1996 | Wenstrom, Jr. ............... | 606/104 |
| 5,562,672 A | 10/1996 | Huebner et al. | |
| 5,569,252 A | 10/1996 | Justin et al. | |
| 5,662,658 A * | 9/1997 | Wenstrom, Jr. ............... | 606/104 |
| 5,723,008 A | 3/1998 | Gordon | |
| 5,730,744 A * | 3/1998 | Justin et al. ..................... | 606/73 |
| 5,843,084 A * | 12/1998 | Hart et al. ........................ | 606/77 |
| 5,897,547 A * | 4/1999 | Schmitz .......................... | 604/391 |
| 6,056,778 A | 5/2000 | Grafton et al. | |
| 6,692,499 B2 * | 2/2004 | Tormala et al. ................. | 606/72 |
| 7,226,468 B2 * | 6/2007 | Ruff .............................. | 606/216 |
| 2002/0052623 A1* | 5/2002 | Whitman ..................... | 606/198 |

FOREIGN PATENT DOCUMENTS

| | | |
|---|---|---|
| EP | 0432320 | 6/1991 |
| EP | 0513736 | 11/1992 |
| EP | 0534152 | 3/1993 |
| EP | 557687 * | 9/1993 |

* cited by examiner

*Primary Examiner* — Katherine Dowe
(74) *Attorney, Agent, or Firm* — Dickstein Shapiro LLP

(57) ABSTRACT

A system and surgical methods for repairing tears in meniscal tissue using meniscal darts. In a preferred embodiment, the system includes a cannulated insertion sheath, a meniscal dart, and a disposable dart driver preloaded with a meniscal dart at its distal end. The insertion sheath is located near a meniscal tear, and sharp prongs on the tip of the sheath are used to secure and position the central fragment of the torn meniscus. The dart driver with a preloaded dart is advanced through the cannulation of the insertion sheath such that the preloaded meniscal dart at the distal end of the driver is inserted through the meniscal tear.

11 Claims, 7 Drawing Sheets

MENISCAL REPAIR SYSTEM AND METHOD

This application claims the benefit of U.S. Provisional Application Ser. No. 60/350,029, filed Jan. 23, 2002, the entire disclosure of which is incorporated herein by reference.

FIELD OF THE INVENTION

The present invention relates to apparatus and techniques for meniscal repair using meniscal darts.

BACKGROUND OF THE INVENTION

The menisci are crescent-shaped structures of fibrocartilaginous tissue located in the knee between the condyles of the tibia and the femur. The menisci, which are actually extensions of the tibia, serve to deepen the tibial plateau to better accommodate the opposing curvature of the articulating surface of the femoral condyle.

A typical injury to the knee is a meniscal tear, which can occur, for example, when the meniscus is displaced and caught between the femoral and tibial condyles during a sudden change of movement of the knee involving a combined flexion-rotation or extension-rotation motion. Meniscal tears were originally treated by removing the meniscus in an operation called a meniscectomy. However, results showed that removing the meniscus, either entirely or even partially, resulted in degenerative arthritis and instability in the knee.

As a result of the above-described complications, surgeons began treating torn meniscus tears with suturing techniques to retain as much of the meniscus as possible. However, suturing of a meniscal tear, like a meniscectomy, was originally an open technique, requiring a large incision and consequently longer periods of rehabilitation and recovery. Advances in instrumentation ultimately led to arthroscopic meniscal repair using long needles for passing suture through the tear.

More recently, various tacks and screws have been developed for meniscal repair, which can be used arthroscopically and simplify the surgery by eliminating the need for suturing altogether. See, for example, U.S. Pat. Nos. 4,873,976; 4,884,572; 4,895,148; 4,924,865; 4,976,715; 5,059,206; 5,125,906; 5,562,672; and 5,569,252. The known tacks and associated surgical methods have various disadvantages, such as the need for special preparation of the meniscus prior to insertion.

SUMMARY OF THE INVENTION

The present invention provides improved systems and surgical techniques for repairing a soft tissue defect, with particular application to defects in the meniscus of a knee.

In one aspect, the present invention provides a disposable meniscal repair assembly comprising a meniscal insertion sheath and a dart stick driver with a preloaded meniscal dart. The disposable dart stick driver is provided with a slit-tube tip for tightly engaging and securing a truncated conical protrusion at the proximal end of the meniscal dart. The dart stick driver is placed within the meniscal insertion sheath and the meniscal dart is manually inserted through an incision in the knee in the proximity of a meniscal tear.

In another aspect, the invention provides a non-disposable meniscal repair assembly comprising a non-disposable joystick handle, a non-disposable insertion sheath attached to the joystick handle and a disposable dart driver having a preloaded dart at one end. The disposable dart driver is provided with a slit-tube tip for tightly engaging and securing a truncated conical protrusion at the proximal end of the meniscal dart. The dart driver with the preloaded dart is placed within the insertion sheath for manual insertion of the dart through an incision in the knee and in the proximity of a meniscal tear.

Alternatively, a non-disposable dart driver may be employed with a non-disposable joystick handle and a non-disposable insertion sheath attached to the joystick handle. According to this embodiment, a meniscal dart is selected and removed from a sterile dart retainer and inserted into the non-disposable insertion sheath. The non-disposable dart driver is then placed within the non-disposable insertion sheath, and the dart is manually inserted through an incision in the knee in proximity of a meniscal tear.

In yet another aspect, the invention provides a method of surgical repair of a soft tissue, such as knee meniscus. An incision is first made in the knee to enable the dart to be arthroscopically positioned proximal and perpendicular to a tear in the meniscus. A meniscal insertion sheath provided with a pointed tip is then inserted through a dart cannula into the joint proximal and perpendicular to the meniscal tear. The central fragment of the torn meniscus is positioned and secured with the pointed tip of the insertion sheath. Either a non-disposable joystick driver or a disposable dart stick driver is then inserted through the insertion sheath. Meniscal repair is accomplished by placing the insertion sheath into the joint. The driver, with the dart in place, is placed into the proximal end of the sheath and advanced until the dart is inserted into the meniscus. The driver is then removed, leaving the dart in place.

These and other features and advantages of the invention will become apparent from the following detailed description that is provided in connection with the accompanying drawings and illustrated exemplary embodiments of the invention.

DETAILED DESCRIPTION OF THE PREFERRED EMBODIMENTS

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Figure 1A:
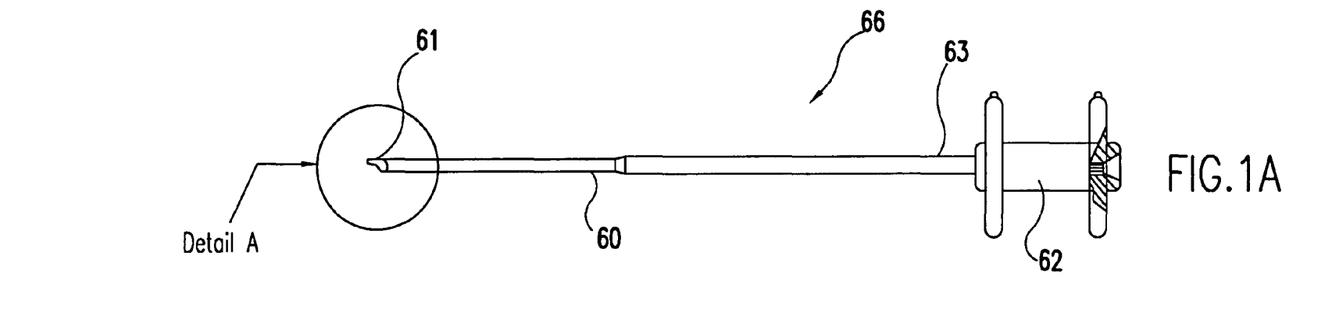
FIG. 1A illustrates a planar view of a straight meniscal dart insertion sheath according to a first embodiment of the present invention.
Figures 1B, 1C:
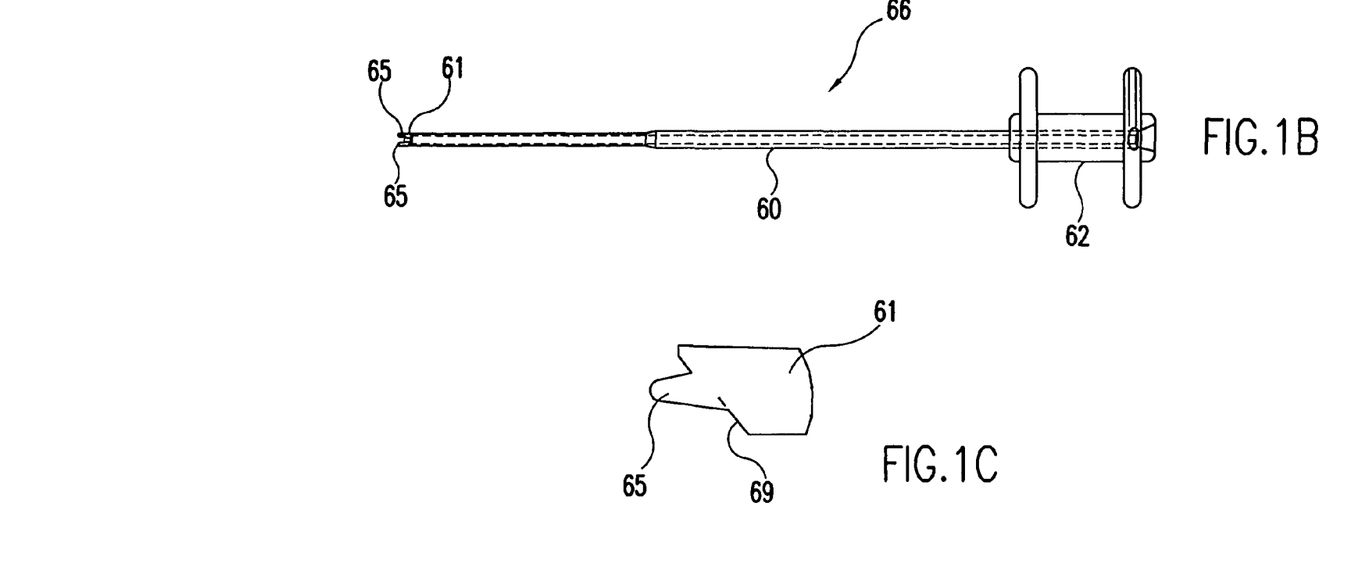
FIG. 1B illustrates a cross-sectional view of the straight meniscal dart insertion sheath of FIG. 1A.
FIG. 1C illustrates a detailed view of the distal end of the straight meniscal dart insertion sheath of FIG. 1A.

Referring now to the drawings, where like elements are designated by like reference numerals, FIGS. 1A-1C illustrate a disposable meniscal dart insertion sheath 66, according to one embodiment of the present invention, and which comprises a proximal end 63, an elongate body 60 and a distal end 61 (shown in greater detail in FIG. 1C). The meniscal dart insertion sheath 66 also comprises an applicator handle 62 located at the proximal end 63 of the elongate body 60, for grasping and insertng the insertion sheath through a dart cannula into a joint.

As depicted in FIG. 1B, which is a cross-sectional view of the insertion sheath 66 of FIG. 1A, distal end 61 comprises a pointed tip 65 for shifting and positioning meniscal tissue from above or below the meniscus prior to the insertion of the dart of the present invention. FIG. 1C depicts in side view the orientation of the pointed tip 65 located on a beveled edge 69. Preferably, the pointed tip 65 comprises two pointed prongs having a pyramidal or tetrahedral configuration, among others, and located symmetrically to each other relative to the longitudinal axis of the insertion sheath 66.

Figure 2A:
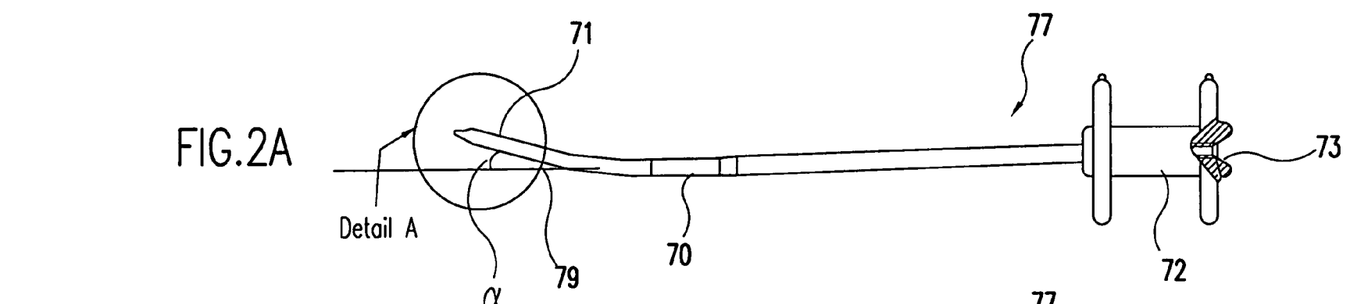
FIG. 2A illustrates a planar view of a 15° meniscal dart insertion sheath according to a second embodiment of the present invention.
Figure 2B:
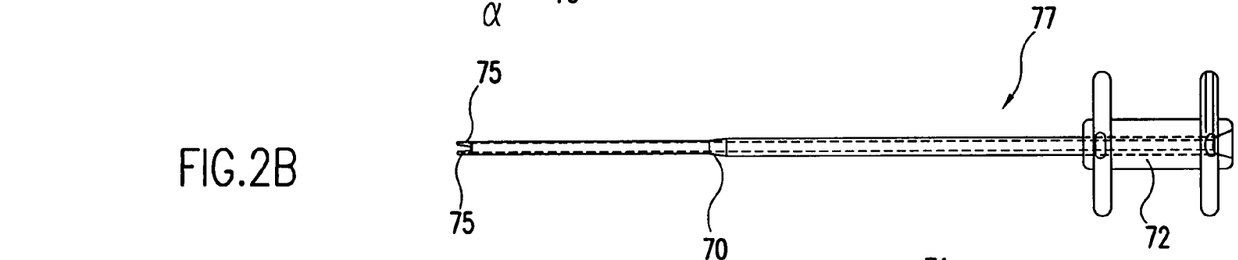
FIG. 2B illustrates a cross-sectional view of the 15° meniscal dart insertion sheath of FIG. 2A.
Figure 2C:
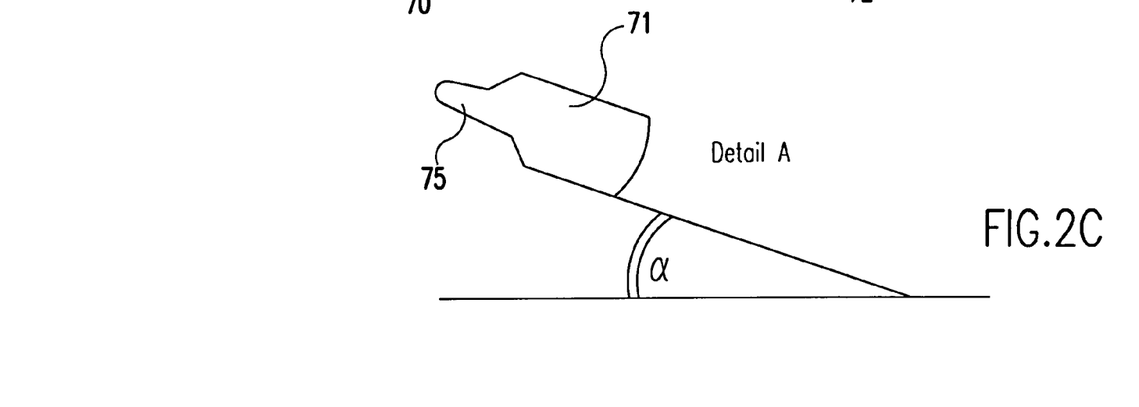
FIG. 2C illustrates a detailed view of the distal end of the 15° meniscal dart insertion sheath of FIG. 2A.

FIGS. 2A-C depict another embodiment of the present invention, according to which meniscal dart insertion sheath 77 of the present invention is provided with an arcuate distal end that forms an angle "α" with the longitudinal axis of the insertion sheath 77. The meniscal dart insertion sheath 77 comprises an elongate body 70, an angled distal end 71 and an applicator handle 72 located at a proximal end 73 of the elongate body 70. In the preferred embodiment of the invention, the angle "α" is about 15 degrees.

FIG. 2B depicts the meniscal dart insertion sheath 77 of FIG. 2A in a cross-section view and rotated 90 degrees. As shown in Detail A of FIG. 2C, the distal end 71 further comprises a pointed tip formed of two pointed prongs as in the straight sheath embodiment of FIGS. 1A-1C.

The elongate body 60, 70 of the meniscal dart insertion sheath 66, 77 may have various cross-sectional shapes and geometries, for example, cylindrical, rectangular, or elipsoidal, among others. The elongate body may be formed of metals and metal alloys, for example, stainless steel and stainless steel alloys, platinum and platinum alloys, gold and gold alloys, nickel and nickel alloys, titanium and titanium alloys, and molybdenum and molybdenum alloys, among others.

If desired, the elongate body 60, 70 of the meniscal dart insertion sheath 66, 77 may be covered with, and insulated by, a dielectric material which may comprise an electrically insulating material such as epoxy, plastic, silicon-based material, ceramic, glass or compositions of these mentioned materials, among many others. The dielectric material may also comprise a perforated shield also formed of an electrically insulating material which may be porous and which may include an opening that allows the elongate body 60, 70 to contact the target meniscal repair.

FIGS. 3A-D illustrate a 12 mm meniscal dart 20 to be employed in conjunction with the meniscal dart insertion sheath 66, 77 of the present invention. Dart 20 of FIGS. 3A-D is similar to the meniscal dart disclosed in U.S. Pat. No. 6,056,778 (the disclosure of which is incorporated herein by reference) to the extent that meniscal dart 20 comprises an elongate body 25 having a pointed distal end 23, a proximal end 21, a central axis 26 along the length of the elongate body 25, and a plurality of lateral grooves 27 disposed along the sides of the elongate body 25. Meniscal dart 20 of FIGS. 3A-D differs, however, from the meniscal dart of U.S. Pat. No. 6,056,778 in that the proximal end 21 is designed to matingly engage a corresponding end of a dart stick driver 50 (FIGS. 4A-C) provided with a slit-tube tip, as described in more detail below. As depicted in Detail A (FIGS. 3A and 3C), the proximal end 21 of meniscal dart 20 terminates in a truncated conical protrusion 22; however, it must be understood that the invention is not limited to this embodiment and contemplates a proximal end of various shapes and geometries, as desired.

Figure 3A:
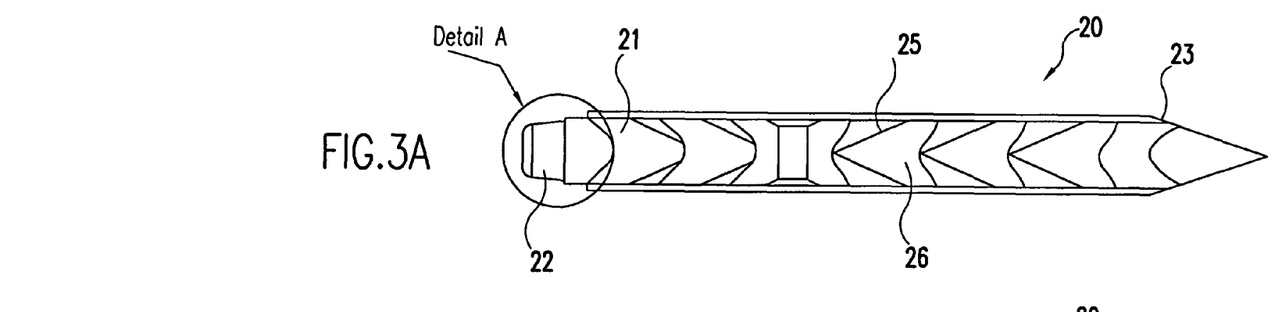
FIG. 3A illustrates a side view of a 12 mm meniscal dart according to the present invention.
Figures 3B, 3C, 3D:
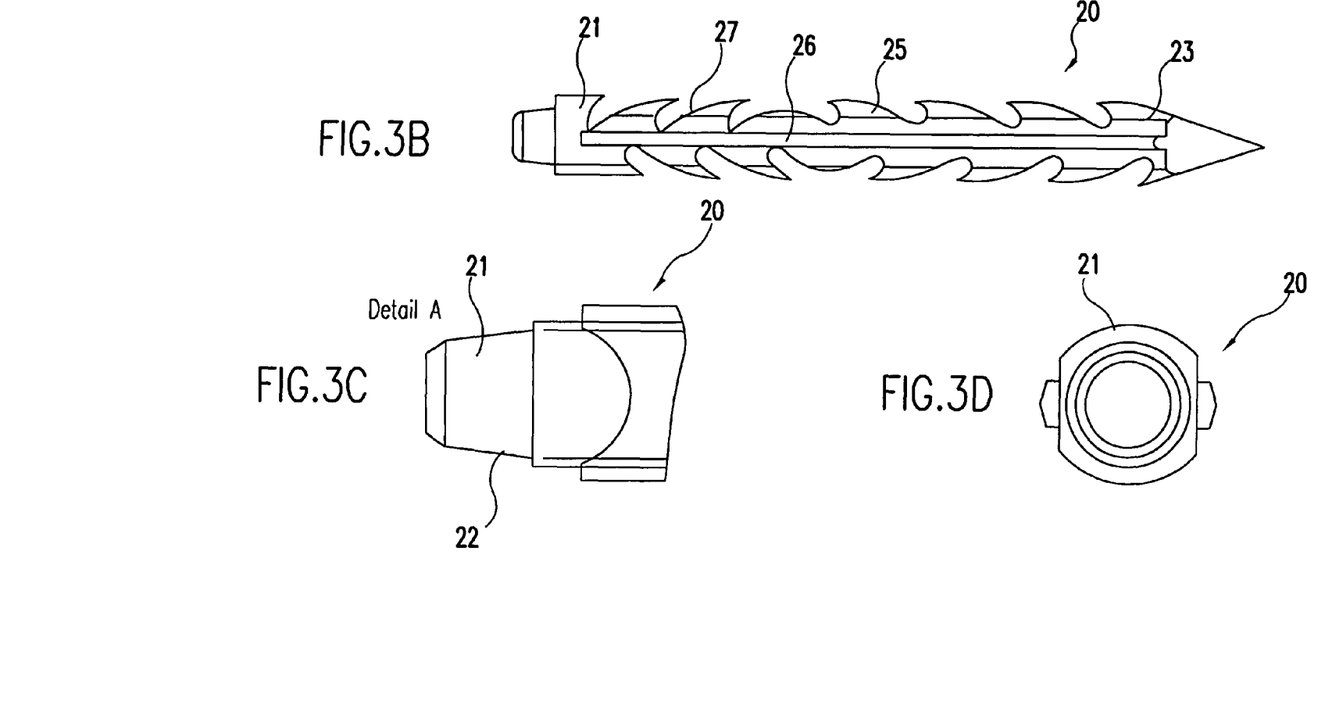
FIG. 3B illustrates a side view of the 12 mm meniscal dart of FIG. 3A rotated 90 degrees.
FIG. 3C illustrates a detailed view of the proximal end of the 12 mm meniscal dart of FIG. 3A.
FIG. 3D illustrates a top view of the proximal end of the 12 mm meniscal dart of FIG. 3A.

FIG. 3B depicts the meniscal dart 20 with lateral grooves 27 disposed along each of the opposing sides, and rotated 90 degrees from the view depicted in FIG. 3A. FIG. 3C provides greater detail of the truncated conical protrusion 22. FIG. 3D illustrates a top view of the truncated conical protrusion 22 of FIG. 3D. Dart 20 of the present invention may be provided in pre-selected sizes, including but not limited to a 10 mm, 12 mm, or 14 mm length (12 mm dart is depicted in FIGS. 3A-D). Preferably, meniscal dart 20 of the present invention is formed of a bioabsorbable material such as PLLA or PLDLA copolymer material. Such PLDLA copolymer material can be completely absorbed within 36 weeks after insertion at a meniscal tear.

Figure 4A:
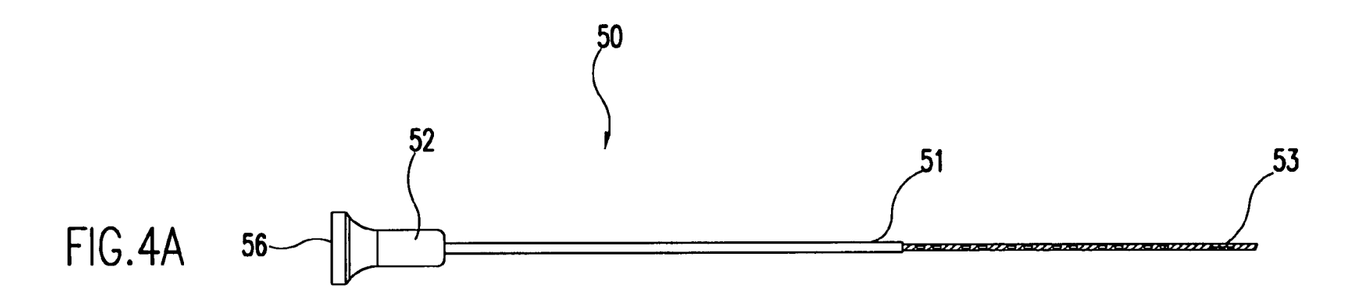
FIG. 4A illustrates a planar view of a meniscal dart stick driver according to the present invention.
Figure 4B:
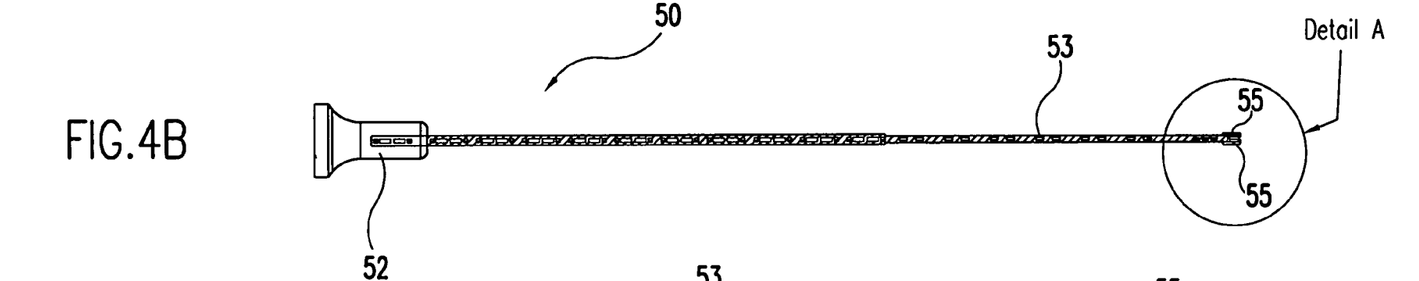
FIG. 4B illustrates a cross-sectional view of the meniscal dart stick driver of FIG. 4A.
Figure 4C:
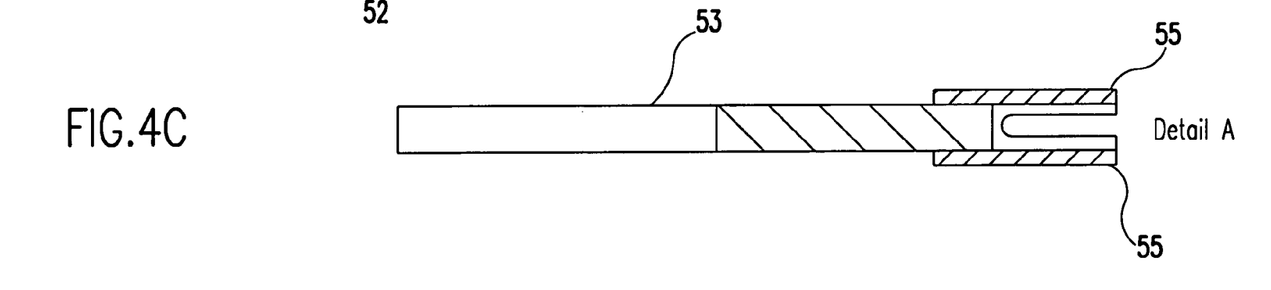
FIG. 4C illustrates a detailed view of the distal end of the meniscal dart stick of FIG. 4A.

FIGS. 4A-C illustrate a disposable meniscal dart driver 50 of the present invention which is employed in conjunction with the meniscal sheath 66 (FIG. 1) and dart 20 (FIG. 3). As shown in FIGS. 4A-B, the meniscal dart driver 50 comprises an elongate shaft 51, a proximal end 56 provided with an elongate section 52, and a distal end 53. The elongate section 52 allows a user, for example a surgeon, to maneuver and operate the dart driver within the meniscal insertion sheath 66 and into the proximity of the meniscal repair by simply using the thumb.

FIG. 4B depicts the meniscal dart driver 50 rotated 90 degrees from the orientation depicted in FIG. 4A. As illustrated in greater detail in Detail A (FIG. 4C), distal end 53 has a slit-tube tip 55 for tightly engaging and accommodating the truncated conical protrusion 22 of the meniscal dart 20 of FIGS. 3A-D.

Figure 5:
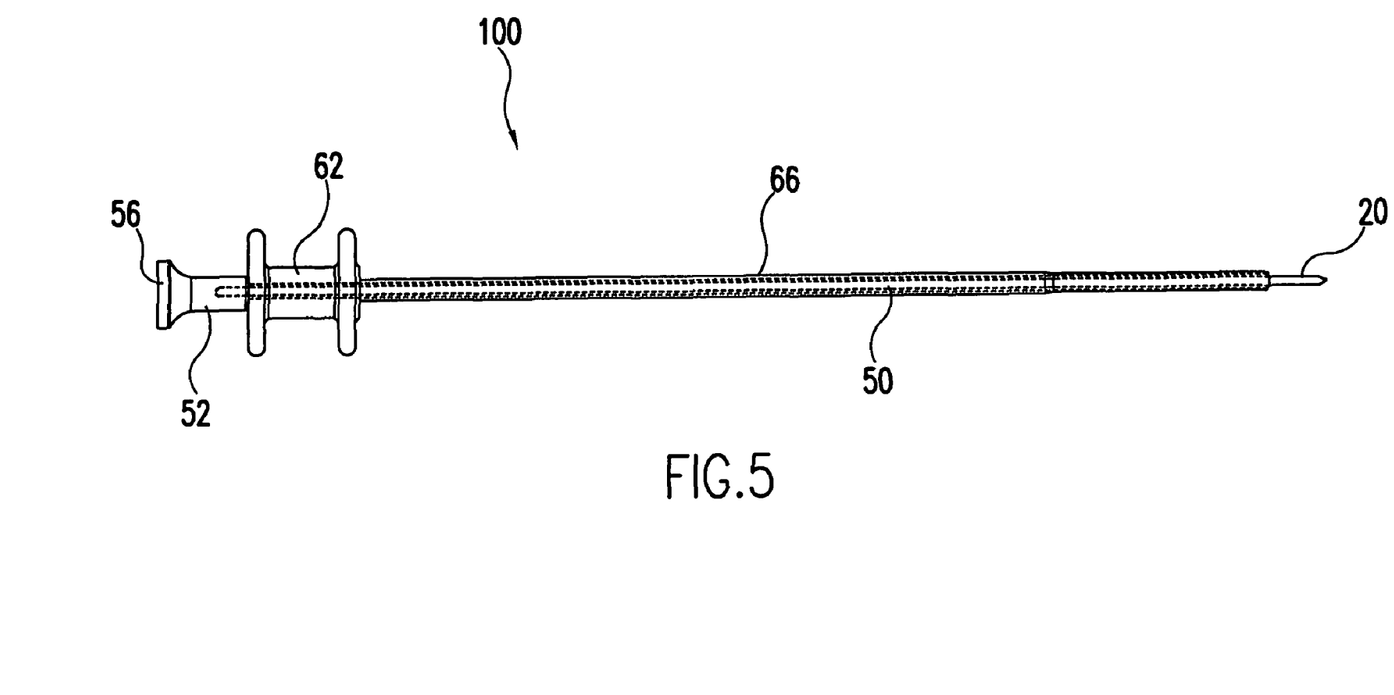
FIG. 5 illustrates a meniscal repair system of the present invention including a meniscal insertion sheath, a preloaded meniscal dart and a dart driver.

FIG. 5 depicts a disposable meniscal repair assembly or system 100 comprising the meniscal straight insertion sheath 66 (FIGS. 1A-C), the meniscal dart stick driver 50 (FIGS. 4A-C) positioned within the insertion sheath 66 and engaging at least one preloaded meniscal dart 20 (FIGS. 3A-D), all in accordance with the present invention. A disposable cannula with an obturator (not shown) may also be provided for use with meniscal repair assembly 100. Preferably, the meniscal repair assembly 100 of the present invention is provided as two pre-packed sterile packs, with five dart and driver units provided in one sterile pack, and five cannula/obturator assemblies provided in a separate sterile pack.

Figure 6A:
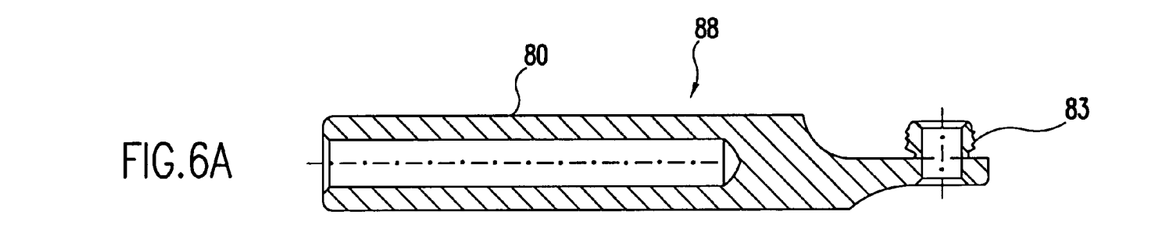
FIG. 6A illustrates a non-disposable joystick handle for attachment of a meniscal insertion sheath according to the present invention.
Figure 6B:
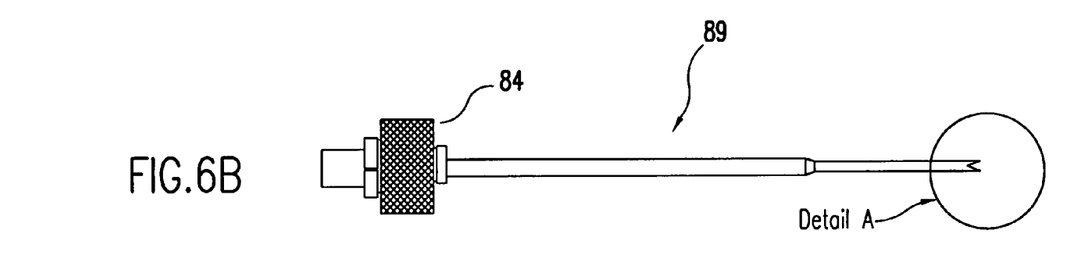
FIG. 6B illustrates a non-disposable insertion sheath which is attachable to the joystick handle of FIG. 6A.
Figure 6C:
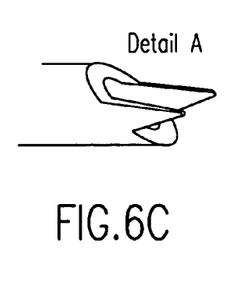
FIG. 6C illustrates a detailed view of the distal end of the insertion sheath of FIG. 6B.

In yet another embodiment of the present invention, a non-disposable meniscal dart insertion sheath may be attached to a non-disposable joystick handle and used with a non-disposable joystick driver in lieu of the disposable dart stick driver 50 of the meniscal repair assembly 100 described above. For example, FIGS. 6A and 6B illustrate, respectively, a non-disposable joystick handle 88 and insertion sheath 89 for the manual insertion of the dart across a meniscal tear. The non-disposable insertion sheath 89 is preferably provided in a straight configuration, as shown in FIG. 6B, and in curved 15° up, 15° up/30° right, 15° up/30° left configurations (not shown). The joystick handle 88 comprises a generally elongate body 80 and a top attachment module 83 which is designed to threadingly engage base 84 of the meniscal insertion sheath 89. Detail A of FIG. 6B shows the pointed barbs on the tip of sheath 89 for engaging and positioning meniscal tissue. After assembly of the handle 88 and sheath 89, a conventional dart (as disclosed in U.S. Pat. No. 6,056,778) is loaded (from a plastic retainer) into sheath 89 and advanced into the meniscus using a non-disposable joystick driver 90, shown in FIG. 6D.

If desired, a trocar 44 (FIG. 6E) may be inserted through the non-disposable meniscal insertion sheath 89 to create a pilot hole prior to the insertion of the darts. This embodiment is especially desirable when tough, calcified meniscal tissue is encountered during meniscal repair operations.

Alternatively, a disposable meniscal dart driver provided with slit-tube tip for securely engaging a meniscal dart, such as the meniscal dart driver 50 (FIG. 4) engaging dart 20 (FIG. 3), can be inserted into the non-disposable sheath 90 attached to the non-disposable joystick handle 89. After insertion of the disposable meniscal dart driver, the meniscal dart is advanced into the meniscus.

The meniscal repair assemblies of the present invention described above with reference to FIGS. 1-6 may be employed in various surgical medical procedures for soft tissue repair. For example the disposable meniscal repair assembly 100 of FIG. 5 may be employed in meniscal tear repairs or repairs of any bodily tissue, such as cartilage, bone, ligaments and skin.

Figures 7A, 7B:
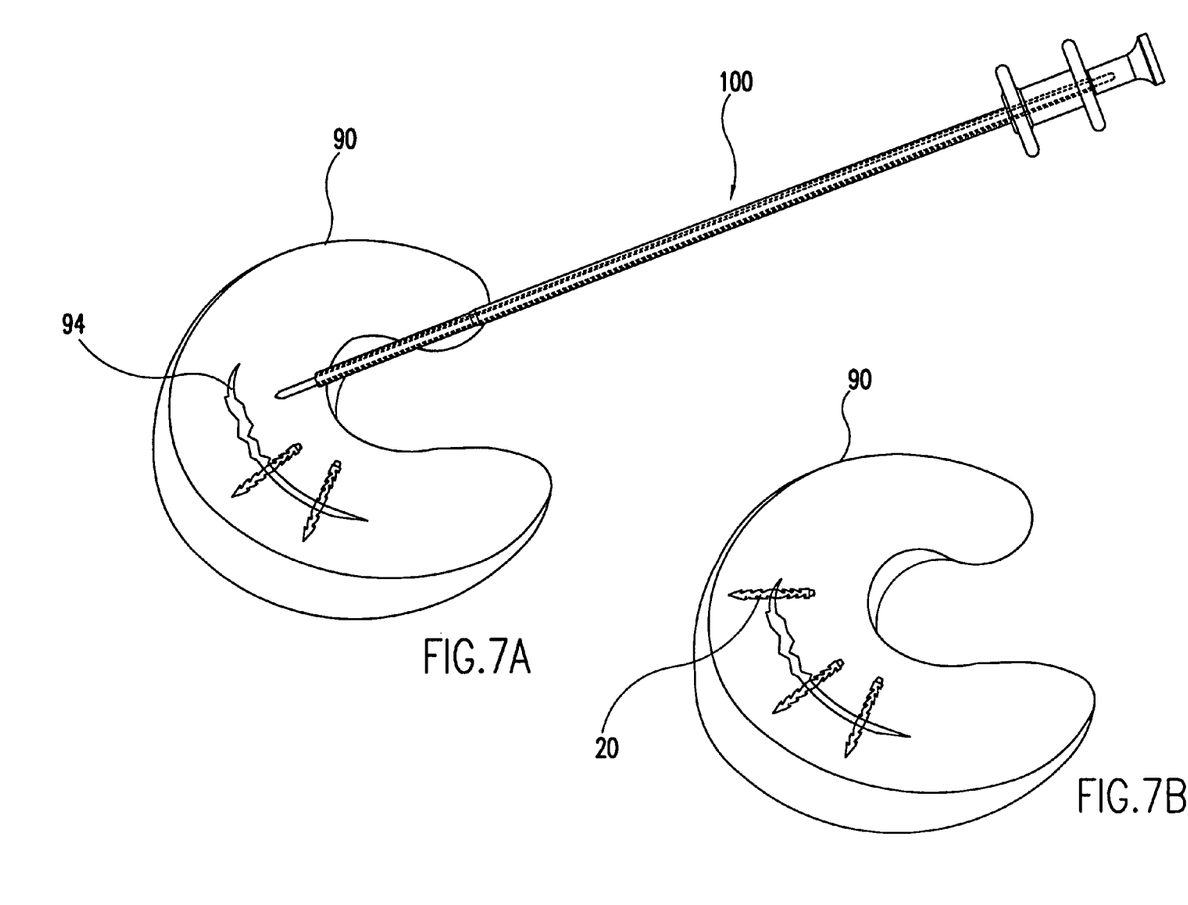
FIG. 7A illustrates a schematic three dimensional view of a knee meniscus undergoing a meniscal repair procedure employing a meniscal repair system of the present invention.
FIG. 7B illustrates the meniscus of FIG. 7A at a stage of meniscal repair subsequent to that shown in FIG. 7A.

To better illustrate an exemplary surgical procedure conducted with the disposable meniscal repair assembly 100 of the present invention, reference is now made to FIG. 7A, which illustrate a three-dimensional view of a knee meniscus 90 provided with meniscal tear 94 to be repaired. The disposable meniscal repair assembly 100 is shown in FIG. 7A in the proximity of the meniscal tear 94.

A preferred method for surgical repair of the meniscal tear 94 according to the present invention commences with standard diagnostic arthroscopy to evaluate the location and extent of meniscal pathology. Meniscal tears located in the vascular zone can also be evaluated with the combination of arthroscopic visualization and a flexible meniscal dart measuring probe. A meniscal vascular punch may be also used to create a bleeding environment in the area of the meniscal tear prior to repair. The punch can be inserted through the tear into the periphery to create an open channel to increase clot formation within the tear. Non-vascular meniscus tears are resected using manual or power instrumentation as necessary.

Upon confirmation of a repairable tear, such as the meniscal tear 94 of FIG. 7A, the peripheral and central edges of the tear may be debrided of fibrous tissue and loose fragments and prepared with a meniscal rasp, for example. This step further stimulates a healing response following dart insertion.

A disposable meniscal dart cannula and obturator (not shown) may be inserted into the anteromedial or anterolateral portal to allow atraumatic insertion of the meniscal repair system 100 of FIG. 5. The flexible cannula and obturator allows the surgeon to accomplish atraumatic arthroscopic insertion of the tip of the insertion sheath 66 into the joint without obstruction by soft tissue. Although the meniscal repair method of the present invention will be described below with reference to a straight mensical insertion sheath, such as the insertion sheath 66 of FIGS. 1 and 5, it must be understood that the invention also contemplates employing a curved insertion sheath, such as the curved insertion sheath 77 of FIG. 2.

Once the insertion sheath 66 has been inserted through the dart cannula, the obturator is removed and a meniscal dart probe is inserted to measure the ideal angle of approach of the dart insertion instrumentation. The probe also measures the meniscus 90 to determine the proper length of the dart 20. Multiple markings located on the meniscal probe serve to determine the appropriate length of the dart 20 necessary to repair the tear 94 in the meniscus 90. The probe is marked at 10, 12 and 14 mm with respect to the corresponding dart sizes available. Thus, the actual size of the dart 20 to be employed in the meniscus repair depends upon the variable width of the meniscus tissue to be repaired. The length of the dart 20 must be also selected such that, when inserted, the dart 20 is entirely contained within the meniscus. The insertion sheath 66 is then positioned to provide recommended meniscal dart placement parallel to the surface of the tibial plateau and perpendicular to the tear 94.

The central fragment of the torn meniscus is secured with the pointed tip 65 of the insertion sheath 66 and positioned into the correct anatomic position for fixation. Care is taken to position the insertion sheath 4 to 6 mm from the tear 94, to provide maximum fixation and apposition of the meniscus once the device is deployed. The dart 20 securely engaged at the tip of the driver 50 is subsequently pushed into the meniscus 90 until the dart is placed beneath the surface of the meniscus and in the meniscal tear 94, as shown in FIG. 7B. Dart placement may be carried out on the femoral or tibial meniscus surfaces as necessary. If desired, multiple darts 20 may be deployed perpendicular to the tear 94, depending on the length of the tear.

A probe is inserted to confirm apposition of the meniscus tear 94 and the complete insertion of the dart 20 (FIG. 7B) within the body of the meniscus tissue. If the dart is not completely inserted, the insertion sheath 66 may be repositioned over the end of the dart and re-driven to complete full insertion of the dart. Final inspection of the meniscus 90 should confirm complete apposition of the tear with no portion of any implant exposed outside of the meniscus. The knee is stabilized in a post-op brace in full extension and patients are instructed to avoid full weight bearing for a minimum of 4 weeks post operatively.

Figures 6D, 6E:
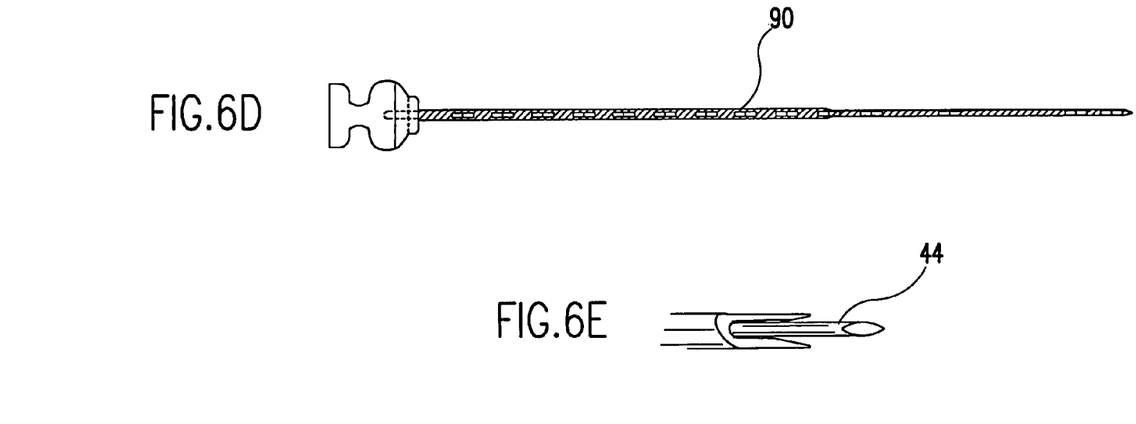
FIG. 6D illustrates a meniscal dart driver insertable in the insertion sheath of FIG. 6B.
FIG. 6E illustrates a detail of the insertion sheath of FIG. 6B, with a trocar protruding from the distal end.

Alternatively, if non-disposable instrumentation is employed, such as the instrumentation shown in FIGS. 6A-6E, then the non-disposable insertion sheath 89 is first secured to the non-disposable joystick handle 88, and then either a disposable meniscal dart driver with an attached dart, such as the meniscal dart driver 50 of FIG. 4 and dart 20 of FIG. 3, or the non-disposable meniscal dart driver 90 of FIG. 6D with a separate conventional dart may be employed. If the non-disposable meniscal dart driver is employed, then the proper meniscal dart is selected and inserted from a sterile dart retainer (not shown) into the sheath.

At this stage, fluid flow from the source (pump or gravity flow system) should be preferably stopped to prevent the dart from being inadvertently pushed out of the insertion sheath. While applying sufficient forward pressure and compression of the reduced meniscus tear, the dart driver is then slid through the insertion sheath, and the dart 20 is pushed into the meniscus 90 until the dart bridges the tear in the meniscus. The handle 88 and insertion sheath assembly are then removed.

Prior to dart insertion, a trocar, such as the trocar 44 of FIG. 6E, may be introduced through the non-disposable insertion sheath and into the meniscus, creating a pilot hole into which dart 20 is deployed. This additional step is performed when it is determined that the meniscus tissue is too rigid to receive a dart without first creating a pilot hole.

Following insertion of an initial dart, the insertion sheath is repositioned, reloaded and the next dart deployed as needed until the meniscus tear is securely repaired. Additional darts are preferably inserted in 5 mm increments over the entire length of the tear. Final inspection of the meniscus should confirm complete apposition of the tear with no portion of any implant exposed outside of the meniscus.

The above description and drawings illustrate preferred embodiments which achieve the objects, features and advantages of the present invention. It is not intended that the present invention be limited to the illustrated embodiments. Any modification of the present invention which comes within the spirit and scope of the following claims should be considered part of the present invention.

What is claimed as new and desired to be protected by Letters Patent of the United States is:

1. A method for repairing a defect in a meniscus comprising the steps of:
    inserting a disposable, elongated, cannulated insertion sheath through an opening in tissue to a location near a torn meniscus;
    providing a disposable device driver, preloaded with a tissue repair device in the form of a dart at its distal end, the tissue repair device comprising an elongated body having a pointed distal tip, a proximal end provided with a protrusion having a truncated conical shape for matingly engaging the device driver, opposing lateral sides, a central axis, and a plurality of lateral grooves having a crescent shape and being disposed along each of the opposing lateral sides of the body, at least two of the lateral grooves having opposite orientations relative to the central axis, the grooves of the tissue repair device forming a regular repeating, longitudinally aligned, non-helical pattern on opposite lateral sides of the elongated body, the pattern on one lateral side of the elongated body being longitudinally offset from the pattern on the opposite lateral side of the body;
    matingly engaging the protrusion at the proximal end of the tissue repair device with a slit-tube at the distal tip of the device driver; and
    inserting the device driver with the tissue repair device engaged by the slit-tube through the cannulation of the insertion sheath, and advancing the device driver and the tissue repair device engaged by the slit-tube through the insertion sheath by using a thumb, such that the thumb directly contacts the proximal end of the device driver, and such that the tissue repair device exits the insertion sheath and is manually inserted and non-rotationally driven into the torn meniscus.

2. The method of claim 1, wherein grooves disposed near the distal tip of the device are angled to open proximally and grooves disposed near the proximal end are angled to open distally, and wherein surfaces of adjacent grooves converge at an acute angle to form sharp edges for anchoring against tissue, the body being configured for the repair of tissue.

3. The method of claim 1, wherein the grooves are formed at an angle of about 30 degrees with respect to the central axis.

4. The method of claim 1, wherein:
    the device driver comprises a body, a distal end and a proximal end, wherein the slit-tube is provided at the distal end of the device drive body; and
    the insertion sheath comprises a body, a distal end and a proximal end, the distal end further comprising a plurality of prongs spaced apart from each other, the body of the insertion sheath being cannulated to receive the device driver.

5. The method of claim 4, wherein the distal end of the insertion sheath is disposed at an angle with respect to the body of the insertion sheath.

6. The method of claim 5, wherein the angle is about 15 degrees.

7. The method of claim 4, wherein the insertion sheath is substantially straight.

8. The method of claim 4, wherein the insertion sheath is coupled to a joystick handle.

9. The method of claim 8, wherein the joystick handle is non-disposable.

10. The method of claim 1, further comprising the step of removing the insertion sheath and the device driver, leaving the tissue repair device in place in the meniscal tear.

11. The method of claim 1, wherein the grooves of the tissue repair device are flexible.

* * * * *